United States Patent
Thrun et al.

(10) Patent No.: US 10,112,882 B2
(45) Date of Patent: Oct. 30, 2018

(54) USE OF NOVEL CYCLIC CARBALDEYDES AS AN AROMATIC SUBSTANCE

(71) Applicant: BASF SE, Ludwigshafen (DE)

(72) Inventors: Frauke Thrun, Mannheim (DE); Joaquim Henrique Teles, Waldsee (DE); Albert Werner, Frankenthal (DE); Richard Dehn, Ludwigshafen (DE); Ralf Pelzer, Fürstenberg (DE); Stephan Maurer, Neustadt (DE)

(73) Assignee: BASF SE, Ludwigshafen am Rhein (DE)

( * ) Notice: Subject to any disclaimer, the term of this patent is extended or adjusted under 35 U.S.C. 154(b) by 17 days.

(21) Appl. No.: 15/514,902

(22) PCT Filed: Sep. 30, 2015

(86) PCT No.: PCT/EP2015/072544
§ 371 (c)(1),
(2) Date: Mar. 28, 2017

(87) PCT Pub. No.: WO2016/050836
PCT Pub. Date: Apr. 7, 2016

(65) Prior Publication Data
US 2018/0230076 A1    Aug. 16, 2018

(30) Foreign Application Priority Data
Sep. 30, 2014    (EP) .................................... 14187075

(51) Int. Cl.
C07C 47/38    (2006.01)
C07C 45/29    (2006.01)
C11B 9/00    (2006.01)

(52) U.S. Cl.
CPC ............. *C07C 47/38* (2013.01); *C07C 45/29* (2013.01); *C11B 9/0038* (2013.01); *C07C 2601/18* (2017.05)

(58) Field of Classification Search
CPC ..... C07C 47/38; C07C 45/29; C07C 2601/18; C11B 9/0038
See application file for complete search history.

(56) References Cited

U.S. PATENT DOCUMENTS 6,903,241 B2    6/2005    Wöhrle et al.
8,212,082 B2    7/2012    Teles et al.
2008/0262452 A1    10/2008    McGinnis et al.
2010/0191018 A1    7/2010    Teles et al.

FOREIGN PATENT DOCUMENTS

EP    1288181 A2    3/2003
WO    WO-2010086313 A1    8/2010
WO    WO-2012084673 A1    6/2012

OTHER PUBLICATIONS

"A new sythesis of aldehydes from ketones utilizing", Database Caplus Accession No. 1994: 434443, XP002736907, 1994.
Dory, Y., et al., "On the Mechanism of the Diehls-Alder Reaction of Enal Dienophiles. Competitive Reactivity and Ab initio Calculations Using a Transannular Probe", Tetrahedron, 1998, vol. 54, pp. 12279-12288.
English Translation of International Preliminary Report on Patentability application No. PCT/EP2015/072544, dated Apr. 6, 2017.
Ihara, M., et al., A Stereoselective Total ,Synthesis of (±)-$\Delta^{8(12)}$- *Capnellene via the Intramolecular Diels-Alder Approach, Journal of the Chemical Society, Chemical Communications*, 1991, pp. 646-647.
Stoll, M., et al., "Contribution á l'étude des combinaisons carbocycliques XXX. La Condensation interne de l 'héxadécane-1, 16-dial et de l'octadécane-1, 18 dial", HELV. CHIM. ACTA, 1937, vol. 20, pp. 525-541.
Tanzer, E-M., et al., "Fluorinated Organocatalysts for the Enantioselective Epoxidation of Enals: Molecular Preogranisation by the Fluorine-Iminium Ion Gauche Effect", Chemistry A European Journal, 2012, vol. 18, pp. 11334-11342.
Thommen, C., et al., "Syntheses of Taiwaniaquinone F and Taiwaniaquinol A via an Unusual Remote C-H Functionalization", Organic Letters, 2013, vol. 15, No. 16, pp. 1390-1393.
International Preliminary Examination Report for PCT/EP2015/072544 (in German) dated Dec. 14, 2016.
International Search Report for PCT/EP2015/072544 dated Dec. 15, 2015.

*Primary Examiner* — Sikarl A Witherspoon
(74) *Attorney, Agent, or Firm* — Drinker Biddle & Reath LLP

(57) ABSTRACT

The present invention relates to new types of cyclic carbaldehydes, the preparation thereof and the use as aromachemical, in particular as fragrance, and to aroma substance compositions and products comprising these carbaldehydes.

14 Claims, 1 Drawing Sheet

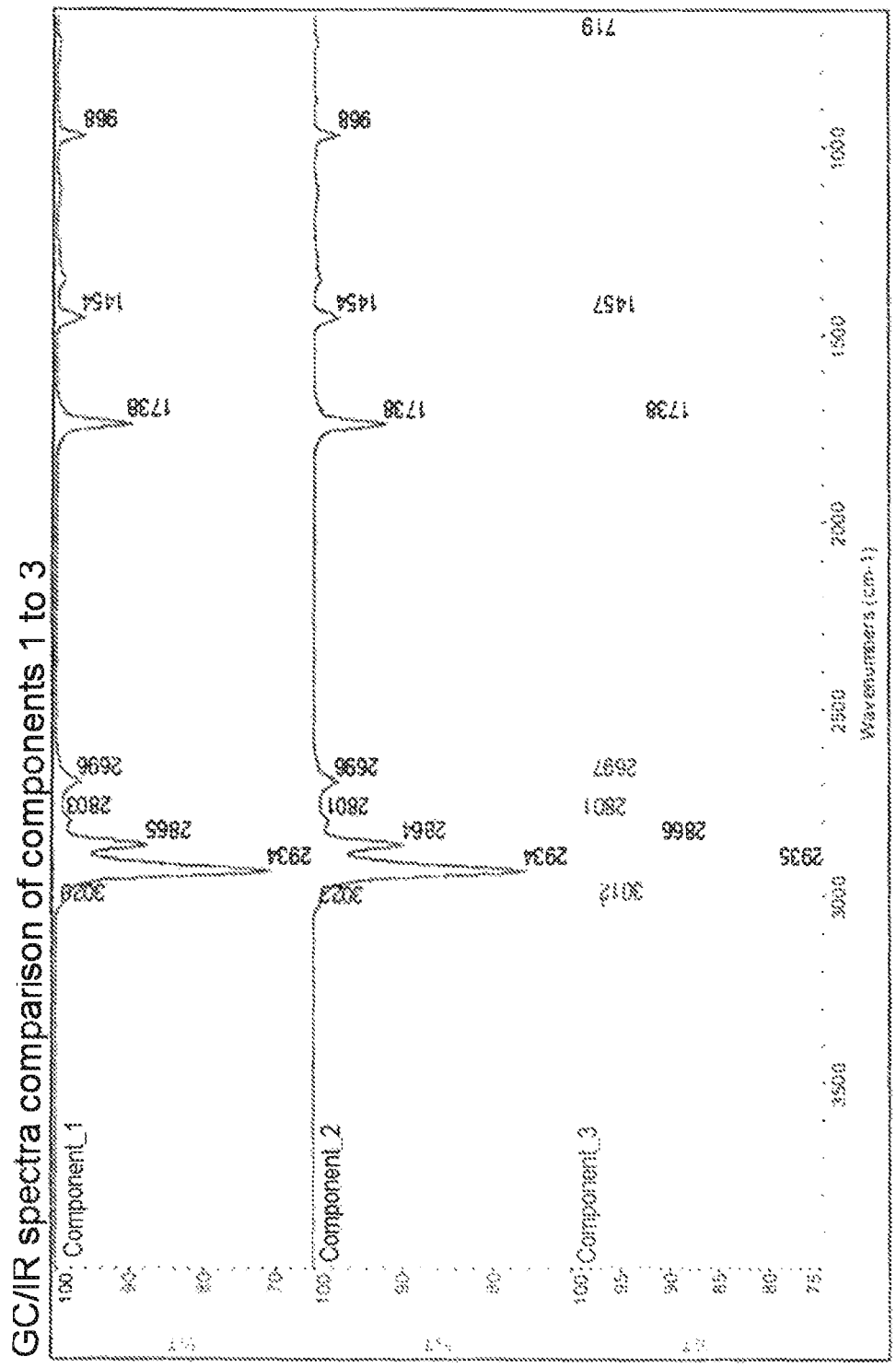

USE OF NOVEL CYCLIC CARBALDEYDES AS AN AROMATIC SUBSTANCE

CROSS-REFERENCE TO RELATED APPLICATIONS

This application is a national stage application (under 35 U.S.C. § 371) of PCT/EP2015/072544, filed Sep. 30, 2015, which claims benefit of European Application No. 14187075.8, filed Sep. 30, 2014, both of which are incorporated herein by reference in their entirety.

The present invention relates to new types of cyclic carbaldehydes, to the preparation thereof and the use as aromachemical, in particular as fragrance, and to aroma substance compositions and products comprising these carbaldehydes.

BACKGROUND OF THE INVENTION

In the perfume industry, there is a constant need for new fragrances which are suitable as fragrance compositions or perfumed articles. The $C_{15}$-aldehydes and the mixtures thereof constitute a contribution to the expansion of the repertoire in the fragrance industry, in particular the musk-like fragrances.

In particular, there is a need for musk-like fragrances and fragrance compositions. This is to be understood as meaning an odor which is similar to the naturally occurring musk scent.

SUMMARY OF THE INVENTION

Surprisingly, the above object was achieved in particular through the provision of carbaldehydes of the formula X described below and primarily through the provision of the specific carbaldehydes of the following formulae I, II and III, which are notable for a marked musk scent:

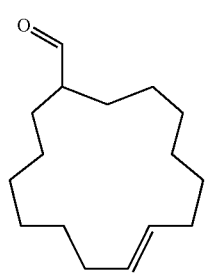

(I)

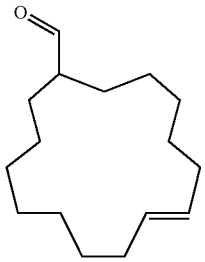

(II)

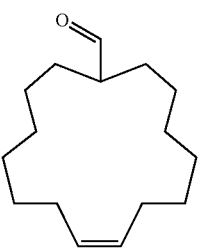

(III)

trans-Cyclopentadec-8-enylcarbaldehyde (I), trans-cyclopentadec-7-enylcarbaldehyde (II) and cis-cyclopentadec-8-enylcarbaldehyde (III) or mixtures thereof, called $C_{15}$-aldehydes below, are not entirely unknown in the literature. During the preparation of cyclohexadec-8-en-1-one by oxidation of cyclohexadec-1,9-diene with nitrous oxide, the $C_{15}$-aldehydes (I), (II) and (III) are produced as byproducts in a ratio 53:1:44. $C_{15}$-Aldehydes (I-Ill) can, moreover, also be prepared starting from cyclohexadec-8-en-1-one by means of a multistage synthesis which comprises a Wolff rearrangement. Besides the already mentioned trans- and cis-$C_{15}$-aldehydes (I) and (III), also the trans-$C_{15}$-aldehyde (II) and also the cis-configuration isomer of (II) are obtained in the process. The isomer distribution of the isolated product mixture obtained by Wolff rearrangement is here 43 (I): 24 (II) 33 (III). It has been found that the $C_{15}$-aldehydes (I-III) have very good olfactory properties. Their odor properties have hitherto not been mentioned in the literature.

DESCRIPTION OF THE FIGURES

FIG. 1 shows the GC/IR spectra of the compounds I, II and Ill according to the invention (referred to therein as components 1, 2 and 3).

DETAILED DESCRIPTION OF THE INVENTION a) General Definitions

An "aroma chemical" is a generic term for compounds which can be used as "fragrance" and/or as "flavoring".

In the context of the present invention, "fragrance" is to be understood as meaning natural or synthetic substances with an intrinsic odor.

In the context of the present invention, "flavoring" is to be understood as meaning natural or synthetic substances with an intrinsic taste.

In the context of the present invention, the "odor" or the "olfactory perception" is the interpretation of the sensory stimuli which are sent from the chemoreceptors in the nose or other olfactory organs to the brain of a living being. The odor can consequently be a sensory perception by the nose of fragrances which takes place upon breathing in. In this case, the air serves as the odor carrier.

In the context of the present invention, "scent" is to be understood as meaning a pleasant smelling odor. The same applies to a "scent substance" according to the invention.

In the context of the present invention, a "perfume" is a mixture of fragrances and carriers, such as in particular an alcohol.

In the context of the present invention, a "perfume composition" is a perfume which comprises different amounts of individual components matched to one another to be in harmony. The properties of the individual constituents are utilized in order to provide a new overall image in the combination, where the characteristics of the ingredients retire into the background, but without being suppressed.

In the context of the present invention, a "perfume oil" is a concentrated mixture of several fragrances which are used e.g. in alcoholic solutions for the perfuming of various products.

In the context of the present invention, a "scent theme" is the predominant scent note in a fragrance composition.

In the context of the present invention, the "top note" is the first phase of the scent progression of a perfume. It plays the decisive role in the first impression, upon opening the bottle and when applying the perfume to the skin. The aim of the top note is to arouse interest in the perfume generally and to ensure attention. Consequently, an extraordinary character is often more important than a polished harmony. The top note is naturally determined by readily volatile fragrances.

In the context of the present invention, "modifying" means to provide the basic theme of a fragrance composition with additional or different accords and odor nuances.

In the context of the present invention, "accords" are produced by combining different fragrances which thus combine to give new odor images. The number of fragrances used can range from two to several hundred.

In the context of the present invention, an "organoleptically/sensorally effective amount" is the amount of a fragrance which suffices to have a stimulatory effect on a sensory organ or stimulatory effect on a sensory receptor.

b) Specific Embodiments of the Invention

The present invention relates in particular to the following subjects:
1. A macrocyclic carbaldehyde of the general formula X

(X)

in which the macrocycle A is a cycloaliphatic hydrocarbon radical with m ring carbon atoms, where m is a whole-numbered value from 13 to 17, such as e.g. 13, 14, 15, 16 or 17, in particular 15, and optionally has n C=C double bonds, where n is a whole-numbered value of 1, 2 or 3, in particular 1, in stereoisomerically pure form or in the form of stereoisomer mixtures, comprising at least two stereoisomeric forms of such a carbaldehyde; and substance mixtures comprising at least 2, such as e.g. 2, 3, 4 or 5, in particular 2 or 3, such carbaldehydes in, in each case, stereoisomerically pure form or as a stereoisomer mixture. Additionally, preference is given to compounds in which, in the case of n=1, the carbaldehyde group and the ring C=C double bond are 4 to 7 ring carbon atoms apart. Substance mixtures can, if n is not 0, also comprise constitutional isomers. If n is 2 or 3, then the double bonds are not cumulated. As shown by the structural formula above, compounds of the formula X are monocyclic carbaldehydes. Preferably, the compounds of the formula X carry no further ring substituents on the macrocycle A besides the carbaldehyde group; it is thus unsubstituted apart from the carbaldehyde group.

2. The compound according to embodiment 1, in which n is 1 and/or m is 15, compounds with n=1 and m=15 being particularly preferred.

3. The compound according to embodiment 2, selected from the isomeric compounds of the formulae I, II and III

(I)

(II)

(III)

and the stereoisomeric forms thereof.

Preferred compounds of the formula X are in particular characterized by the following sets of analytical data:

Set 1:
$^1$H NMR (500 MHz, CDCl$_3$, 25° C.): σ=9.5 (s, CHO, 1H), 5.4-5.3 (m, HC=CH, 2H), 2.4-2.3 (m, 1H), 2.2-1.9 (m, 4H), 1.7-1.6 (m, 2H), 1.5-1.1 (m, 18H).
$^{13}$C-NMR (125 MHz, CDCl$_3$, 25° C.): 6=206.0 (C=O), 131.2 (HC=CH), 48.4 (CH), 31.6 (2×CH$_2$), 28.3 (2×CH$_2$), 27.0 (2×CH$_2$), 26.7 (2×CH$_2$), 26.6 (2×CH$_2$), 25.1 (2×CH$_2$).
IR (GC/IR) υ [cm$^{-1}$]=3029 (1,2 trans subst. DB), 2934, 2865, 2797, 2695, 1738 (CHO), 1454, 1353, 1110, 968 (1,2 trans subst. DB).

Set 2:
IR (GC/IR) υ [cm$^{-1}$]=3023 (trans 1,2 subst. DB), 2934, 2864, 2801, 2696, 1738 (CHO), 1454, 968 (trans 1,2 subst. DB).
MS (GC/MS-IR coupling) m/z=236.

Set 3:
IR (GC/IR) υ [cm$^{-1}$]=3012 (1,2 cis subst., DB), 2935, 2866, 2801, 2698, 1738 (CHO), 1457, 719 (1,2 cis subst. DB).
MS (GC/MS-IR coupling) m/z=236.

The invention thus provides in particular compounds according to embodiment 2, characterized by one of the above analytical data sets 1, 2 and 3.

Such substances are e.g. accessible by a process according to the following embodiments 13 to 17 or by a process of embodiments 18 to 20.

The invention furthermore provides compounds according to embodiments 1 to 3, obtainable according to example 1 and optionally followed by a purification according to examples 3 and 4 of the experimental section of the present description.

The invention furthermore provides compounds according to embodiments 1 to 3, obtainable according to example 2 and optionally followed by a purification according to examples 3 and 4 of the experimental section of the present description.

The invention furthermore provides compounds according to embodiments 1 to 3, obtainable according to example 5 (stages 1 to 5) and optionally followed by a purification according to example 5 (stage 6) of the experimental section of the present description.

4. A substance mixture comprising at least one, such as in particular 2, 3 or 4, preferably 2 or 3, compound(s) according to one of embodiments 1 to 3.

Such substance mixtures are e.g. accessible by a process according to the following embodiments 13 to 17 or by a process of embodiments 18 to 20.

The invention furthermore provides such substance mixtures obtainable by example 1 and optionally followed by a purification according to examples 3 and 4 of the experimental section of the present description.

The invention furthermore provides such substance mixtures obtainable by example 2 and optionally followed by a purification according to examples 3 and 4 of the experimental section of the present description.

The invention furthermore provides such substance mixtures obtainable by example 5 (stages 1 to 5) and optionally followed by a purification according to example 5 (stage 6) of the experimental section of the present description.

Also encompassed according to the invention are substance mixtures comprising the 7-cis analogon of the compound of the formula II, i.e. cis-cyclopentadec-7-enylcarbaldehyde and the use thereof, as defined herein.

Also encompassed according to the invention is the 7-cis analogon of the compound of the formula II, i.e. cis-cyclopentadec-7-enylcarbaldehyde and the use thereof as defined herein.

5. The use of at least one substance or substance mixture according to one of the preceding embodiments as aromachemical, in particular as fragrance.

6. The use according to embodiment 5 in products selected from perfumes, detergents and cleaners, cosmetic products, body care products, hygiene articles, foods, food supplements, air fresheners, scent substances, pharmaceutical products and crop protection products.

7. The use according to either of embodiments 5 and 6 of a mixture essentially comprising trans-cyclopentadec-8-enylcarbaldehyde (I).

8. The use according to embodiment 7 of a mixture comprising trans-cyclopentadec-8-enylcarbaldehyde (I), trans-cyclopentadec-7-enylcarbaldehyde (II) and cis-cyclopentadec-8-enylcarbaldehyde (III), where the fraction of trans-cyclopentadec-8-enylcarbaldehyde (I) in the mixture based on the sum of the components of the formulae I, II and III is at least 65%, such as e.g. 65-100%, 75-98% or 85-95%.

9. The use according to embodiment 5 or 6 of a mixture comprising the compounds of the formulae I, II and III, where the weight ratio of I:II:III is in the range from 0.3-0.5:0.2-0.3:0.3-0.4.

10. The use according to embodiment 9 of a mixture comprising the compounds of the formulae I, II and III in a weight ratio of I:II:III of about 43:24:33.

11. The use according to any one of embodiments 5 to 10 for producing a musk note in a fragrance composition.

12. The use according to embodiment 11 for conveying, modifying and/or boosting a musk scent note in a fragrance composition by admixing a sensorally effective amount of at least one substance or a substance mixture according to the definition in any one of embodiments 1 to 10.

13. A process for the preparation of a compound of the general formula X

in which A is a cycloaliphatic hydrocarbon radical with m ring carbon atoms, where m is a whole-numbered value from 13 to 17, such as e.g. 13, 14, 15, 16 or 17, in particular 15, and optionally has n C=C double bonds, where n is a whole-numbered value of 1, 2 or 3, where a) a cycloaliphatic compound of the formula XI

in which A' is a cycloaliphatic hydrocarbon radical with m+1 ring carbon atoms, where m is a whole-numbered value from 13 to 17, and optionally has n+1 C=C double bonds, where n is a whole-numbered value of 1, 2 or 3, in particular 1, which radical is oxidized with dinitrogen monoxide ($N_2O$); and b) at least one compound of the formula X are isolated from the reaction mixture.

14. The process according to embodiment 13, where the compound of the formula X is isolated by distillation and optionally subsequent chromatography.

15. The process according to embodiment 13 or 14, where the starting material of the formula XI used is a cyclohexadeca-1,9-diene, and trans- and cis-cyclopentadec-8-enylcarbaldehyde (I, III) and/or trans-cyclopentadec-7-enylcarbaldehyde (II) are isolated.

16. The process according to any one of embodiments 13 to 15, where the compound of the formulae (I)-(III) is isolated by means of fractional distillation from a reaction mixture in which the weight ratio of the $C_{15}$-aldehydes (I)-(III) to cyclohexadeca-1,9-diene is at least 0.01, such as e.g. 0.01-0.1, 0.03-0.095 or 0.06-0.09.

17. The process according to any one of embodiments 13 to 15, where trans-cyclopentadec-8-enylcarbaldehyde (I) is isolated by means of chromatic purification from a mixture which has been obtained by fractional distillation and has a content of (I)-(III) in total of at least 5% by weight, such as e.g. 5-50%, 20-48 or 30-45%.

18. A process for the preparation of a compound of the general formula X

(X)

in which A is a cycloaliphatic hydrocarbon radical with m ring carbon atoms, where m is a whole-numbered value from 13 to 17, and optionally has n C=C double bonds, where n is a whole-numbered value of 1, 2 or 3, where a) a cycloaliphatic compound of the formula XII

(XII)

in which A' is a cycloaliphatic hydrocarbon radical with m+1 ring carbon atoms, where m is a whole-numbered value from 13 to 17, such as e.g. 13, 14, 15, 16 or 17, in particular 15, and optionally has n+1 C=C double bonds, where n is a whole-numbered value of 1, 2 or 3, in particular 1, is reacted with NaH and methyl formate to give the corresponding cyclic formylketone XIII

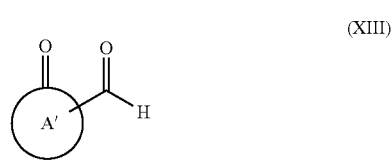

(XIII)

in which A' is as defined above, where keto group and formyl group are preferably bonded to adjacent ring carbon atoms;

b) the formed formylketone is reacted with triethylamine and 4-acetamidobenzyl azide to give the corresponding diazoketone XIV;

(XIV)

in which A' is as defined above, where keto group and diazo group are preferably bonded to adjacent ring carbon atoms;

c) N$_2$ is cleaved off from the formed diazoketone under the conditions of a Wolff rearrangement and reacted in the presence of an alcohol to give the corresponding ester of the formula XV

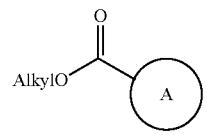

(XV)

in which A is as defined above;

d) the thus formed ester is reduced to the corresponding alcohol XVI

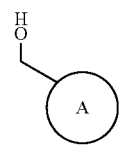

(XVI)

in which A is as defined above;

e) the thus formed alcohol is oxidized to the carbaldehyde of the formula X;

f) and optionally the carbaldehyde of the formula X is isolated from the reaction mixture, 19. The process according to embodiment 18, where cis-/trans-cyclohexadec-8-enone is used as compound of the formula XI in stage a), and trans-cyclopentadec-8-enylcarbaldehyde (I), trans-cyclopentadec-7-enylcarbaldehyde (II) and cis-cyclopentadec-8-enylcarbaldehyde (III) are obtained in stage e).

20. The process according to embodiment 15, where compounds of the formula (I), (II) or (III) or mixtures thereof are obtained in stage f) by chromatic purification of a reaction mixture from stage e), where the content thereof of (I), (II) and (Ill) is in total preferably at least 50% by weight, such as e.g. 50-100% by weight, 60-99% by weight or 70-95% by weight.

21. A fragrance composition comprising at least one substance or a substance mixture according to the definition in any one of embodiments 1 to 10 or prepared by any one of the processes according to embodiments 13 to 20.

22. The composition according to embodiment 21, comprising the substance or the substance mixture in a weight fraction of from 0.01 to 99.9% by weight, based on the total weight of the composition.

23. A product comprising at least one substance or a substance mixture according to the definition in any one of embodiments 1 to 10 or prepared by any one of the processes according to embodiments 13 to 20.

24. The product according to embodiment 23, comprising the substance or the substance mixture in a weight fraction of from 0.01 to 99.9% by weight, 1 to 80% by weight, 2 to 50% by weight, 3 to 25 or 5 to 15% by weight, based on the total weight of the composition.

25. The product according to embodiment 23 or 24, selected from perfumes, detergents and cleaners, cosmetic products, body care products, hygiene articles, foods, food supplements, air fresheners, scent substances, pharmaceutical products and crop protection products.

26. The substance mixture according to embodiment 4, obtainable by a process according to any one of embodiments 13 to 17 or in particular 18 to 20.

c) Further Configurations of the Invention c1) Fragrance Compositions:

According to a further aspect, the fragrances used according to the invention are used, especially for the purpose of more efficient handling and metering, also as fragrance mixtures with diluents or solvents. Here, the fraction of the fragrances, based on the sum of fragrances and solvents, is given in % by weight.

Solvent:

In the context of the present invention, a "solvent" serves for the dilution of the fragrances to be used according to the invention or of the fragrance composition according to the invention without having its own odiferous properties. Some solvents have fixing properties at the same time.

The compound of the formula (X) according to the invention or an above-defined substance mixture of two or more compounds/isomers of the formula (X) can be admixed to a diluent or solvent in 0.1 to 99% by weight. Preference is given to at least 40% strength by weight solutions, further preferably at least 50% strength by weight solutions, furthermore preferably at least 60% strength by weight solutions, further preferably at least 70% strength by weight solutions, particularly preferably at least 80% strength by weight solutions, furthermore particularly preferably at least 90% strength by weight solutions, preferably in olfactorily acceptable solvents.

Preferred olfactorily acceptable solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), benzyl benzoate (BB) and benzyl acetate. Here, preference is in turn given to ethanol, diethyl phthalate, propylene glycol, dipropylene glycol, triethyl citrate, benzyl benzoate and isopropyl myristate.

In the context of the present invention, a "fragrance composition" is a mixture which comprises at least one further fragrance alongside a compound of the formula (X) according to the invention or an above-defined substance mixture of two or more compounds/isomers of the formula (X). In particular, such a fragrance composition can be a perfume composition (a perfume oil).

Fragrance compositions according to the invention comprise, based on the total amount of the fragrance composition, e.g. an amount of a compound of the formula (X) according to the invention or of an above-defined substance mixture of two or more compounds/isomers of the formula (X) of from 0.01 to 65% by weight, preferably from about 0.1 to about 50% by weight, preferably from about 0.5 to about 30% by weight and particularly preferably from about 0.5 to about 25% by weight. The weight ratio of compound/compounds of the formula X according to the invention to the total amount of further fragrances is e.g. in the range from 1:1000 to 1:0.5, preferably in the range from 1:700 to 1:1, particularly preferably in the range from 1:500 to 1:10.

Fragrance compositions according to the invention comprise, based on the total amount of the fragrance composition, e.g. an amount of compound/compounds of the formula X according to the invention of from 0.01 to 65% by weight, preferably from about 0.1 to about 50% by weight, preferably from about 0.5 to about 30% by weight and particularly preferably from about 0.5 to about 25% by weight. The weight ratio of compound/compounds of the formula X according to the invention to the total amount of further fragrances (different therefrom) is e.g. in the range from 1:1000 to 1:0.5, preferably in the range from 1:700 to 1:1, particularly preferably in the range from 1:500 to 1:10.

Further Fragrances:

Besides the compound/compounds of the formula X according to the invention, fragrance compositions according to the invention comprise at least one further fragrance, preferably 2, 3, 4, 5, 6, 7, 8 or more further fragrances, where further fragrances are selected e.g. from among:

Alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lilial[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide'), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone[1951 5]), 3,3,5-trimethylcyclohexyl acetate (preferably with a content of cis isomers of 70% by weight or more) and 2,5,5-trimethyl-1,2,3,4,4a,5,6,7-octahydronaphthalen-2-ol (Ambrinol S[1]). Within the context of the present invention, the aforementioned fragrances are accordingly preferably combined with mixtures according to the invention.

Where trade names are given above, these refer to the following sources:

[1] trade name of Sym rise GmbH, Germany;
[2] trade name of Givaudan AG, Switzerland;
[3] trade name of International Flavors & Fragrances Inc., USA;
[5] trade name of Danisco Seillans S.A., France;
[9] trade name of Firmenich S.A., Switzerland;
[10] trade name of PFW Aroma Chemicals B.V., the Netherlands.

Further fragrances with which the (E/Z)-cyclopentadecenylcarbaldehydes (I)-(III) can be combined e.g. to give a fragrance composition can be found e.g. in S. Arctander, Perfume and Flavor Chemicals, Vol. I and II, Montclair, N.J., 1969, self-published, or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; spruce needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; ylang ylang oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanal; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethyl-cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1- ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanenitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

c2) Fragrance-Containing Articles

Cyclopentadecenylcarbaldehydes of the formulae (I)-(III) according to the invention or fragrance compositions according to the invention can be incorporated into a series of products or be applied to such products.

Fragrances according to the invention can be used in the production of perfumed articles. The olfactory properties, like the material properties (such as solubility in customary solvents and compatibility with further customary constituents of such products), as well as the toxicological acceptability of the fragrances according to the invention underline their particular suitability for the stated use purposes. The positive properties contribute to the fact that the fragrances used according to the invention and the fragrance compositions according to the invention are particularly preferably used in perfume products, body care products, hygiene articles, textile detergents, and in cleaners for solid surfaces.

The perfumed article is e.g. selected from perfume products, body care products, hygiene articles, textile detergents and cleaners for solid surfaces. Preferred perfumed articles according to the invention are also selected from among:

perfume products selected from perfume extracts, Eau de Parfums, Eau de Toilettes, Eau de Colognes, Eau de Solide, Extrait Partum, air fresheners in liquid form, gel-like form or a form applied to a solid carrier, aerosol sprays, scented cleaners and oils;

body care products selected from aftershaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, hair shampoo, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics such as e.g. eyeshadows, nail varnishes, make-ups, lipsticks, mascara, toothpaste, dental floss;

hygiene articles selected from candles, lamp oils, joss sticks, insecticides, repellents, propellants, rust removers, perfumed freshening wipes, armpit pads, baby diapers, sanitary towels, toilet paper, cosmetic wipes, pocket tissues, dishwasher deodorizer;

cleaners for solid surfaces selected from perfumed acidic, alkaline and neutral cleaners, such as e.g. floor cleaners, window cleaners, dishwashing detergents, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners;

textile detergents selected from liquid detergents, powder detergents, laundry pretreatments such as bleaches, soaking agents and stain removers, fabric softeners, washing soaps, washing tablets.

According to a further aspect, the fragrances used according to the invention and the fragrance compositions according to the invention are suitable for use in surfactant-containing perfumed articles. This is because fragrances and/or fragrance compositions with a musk note and pronounced naturalness are often sought—especially for the perfuming of surfactant-containing formulations such as, for example, cleaners (in particular dishwashing compositions and all-purpose cleaners).

According to a further aspect, fragrances used according to the invention and fragrance compositions according to the invention can be used as agents for providing (a) hair or (b) textile fibers with a rosy odor note.

The fragrances to be used according to the invention and fragrance compositions according to the invention are therefore particularly well suited for use in surfactant-containing perfumed articles.

It is preferred if the perfumed article is one of the following:

an acidic, alkaline or neutral cleaner which is selected in particular from the group consisting of all-purpose cleaners, floor cleaners, window cleaners, dishwashing detergents, bath and sanitary cleaners, scouring milk, solid and liquid toilet cleaners, powder and foam carpet cleaners, liquid detergents, powder detergents, laundry pretreatments such as bleaches, soaking agents and stain removers, fabric softeners, washing soaps, washing tablets, disinfectants, surface disinfectants, an air freshener in liquid form, gel-like form or a form applied to a solid carrier or as an aerosol spray, a wax or a polish, which is selected in particular from the group consisting of furniture polishes, floor waxes and shoe creams, or a body care composition, which is selected in particular from the group consisting of shower gels and shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, aftersun creams and lotions, hand creams and lotions, foot creams and lotions, hair removal creams and lotions, aftershave creams and lotions, tanning creams and lotions, hair care products such as e.g. hairsprays, hair gels, setting hair lotions, hair conditioners, permanent and semipermanent hair colorants, hair shaping compositions such as cold waves and hair smoothing compositions, hair tonics, hair creams and hair lotions, deodorants and antiperspirants such as e.g. underarm sprays, roll-ons, deodorant sticks, deodorant creams, products of decorative cosmetics.

Ingredients with which fragrances used according to the invention or fragrance compositions according to the invention can preferably be combined are, for example: preservatives, abrasives, antiacne agents, agents to combat skin aging, antibacterial agents, anticellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emollients, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, ° pacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, detergents, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, aromas, flavorings, fragrances, polyols, surfactants, electrolytes, organic solvents or silicone derivatives.

According to a further aspect, the fragrances are used in the production of the perfumed articles in liquid form, undiluted or diluted with a solvent or in the form of a fragrance composition. Suitable solvents for this purpose are e.g. ethanol, isopropanol, diethylene glycol monoethyl ether, glycerol, propylene glycol, 1,2-butylene glycol, dipropylene glycol, diethyl phthalate, triethyl citrate, isopropyl myristate, etc. If the specified solvents have their own olfactory properties, they are assigned exclusively to the constituent "solvent" and not to the "fragrances".

The fragrances and/or fragrance compositions present in the perfumed articles according to the invention can in this connection, in one embodiment, be absorbed onto a carrier, which ensures both fine distribution of the fragrance or fragrance composition within the product and controlled release upon use. Carriers of this type may be porous inorganic materials such as light sulfate, silica gels, zeolites, gypsums, clays, clay granules, aerated concrete, etc. or organic materials such as woods and cellulose-based materials.

The fragrances used according to the invention and the fragrance compositions according to the invention can also be in microencapsulated form, spray-dried form, in the form of inclusion complexes or in the form of extrusion products and be added in this form to the product or article to be perfumed. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the perfume oil, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting fragrances used according to the invention and fragrance compositions according to the invention with a suitable wax-like substance and by extrusion with subsequent solidification, optionally in a suitable solvent, e.g. isopropanol.

c3) Preparation of Fragrances According to the Invention

The carbaldehydes according to the invention of the formula X

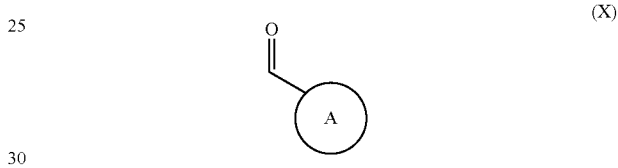

(X)

in which A is as defined above and is a cyclic $C_{13}$ to $C_{17}$ radical, in particular $C_{13}$-, $C_{15}$-, or $C_{17}$ radical, are obtainable starting from cyclic ketones or cyclic olefin starting materials known per se.

The following synthesis routes are described in more detail by way of example to further illustrate the invention:

Synthesis Route 1: Carbaldehyde Synthesis by $N_2O$ Oxidation

Starting from the corresponding, aliphatic carbocycle, in particular a cyclic mono- or polyunsaturated olefin XI (i.e. compared to the cyclic radical A in the product of the formula X, the starting compound XI comprises an additional C=C double bond and an additional carbon atom in the ring), compounds of the formula X are accessible by dinitrogen monoxide oxidation, as described e.g. in WO2010/086313.

An example of a suitable starting compound (which can be used both in stereoisomerically pure form as well as in the form of stereoisomer mixtures) for the preparation of compounds of the formula (X), in which A is a monounsaturated $C_{15}$ radical, is cyclohexadeca-1,9-diene, which is either commercially available or can be prepared according to example 2 of WO 2012/084673 or in accordance with EP-A-1 288 181.

In particular here, a cyclic olefin is oxidized by reaction with dinitrogen monoxide. Dinitrogen monoxide here can be used in pure form or optionally in a mixture with other substances gaseous under reaction conditions, such as e.g. carbon dioxide, for dilution.

In this connection, the reaction of the cyclic olefin with dinitrogen monoxide can take place without a diluent or in the presence of at least one suitable solvent or diluent. Preferably, the reaction takes place without a diluent. Essentially all customary solvents and/or diluents are suitable here, but with the proviso that they have neither a C—C double bond nor a C—C triple bond, nor an aldehyde group.

Suitable solvents to be mentioned include: cyclic alkanes, for example cyclohexane, cyclopentane, cyclooctane, cyclododecane or saturated aliphatic or aromatic, optionally alkyl-substituted hydrocarbons.

The temperature during the reaction is e.g. 140 to 350° C., such as in particular 180 to 320° C. or 200 to 300° C. It is also possible to carry out the reaction at two or more temperatures or in two or more temperature ranges which are in each case within the limits stated above. Temperature changes in the course of the reaction can be completed continuously or else discontinuously. In particular, however, the reaction temperature is essentially constant.

The pressure during the reaction of the cyclic olefin with dinitrogen monoxide is in particular higher than the intrinsic pressure of the starting material or product mixture at the selected reaction temperature or the selected reaction temperatures. The pressure is e.g. 1 to 1000 bar, such as e.g. 40 to 300 bar or 50 to 200 bar.

It is possible to carry out the reaction of the cyclic olefin with dinitrogen monoxide at two or more pressures or within two or more pressure ranges which are in each case within the limits stated above. Pressure changes in the course of the reaction can be completed continuously or else discontinuously. In particular, however, the pressure during the reaction is essentially constant.

As regards the reactors that can be used for the reaction (in the laboratory—or production scale), there are no particular limitations. In particular, the reaction can take place in a batch procedure or continuous procedure. Consequently, examples of reactors that can be used are at least one CSTR (Continuous Stirred Tank Reactor) with at least one internal and/or at least one external heat exchanger, at least one tubular reactor, at least one tube-bundle reactor or at least one loop reactor. It is likewise possible to configure at least one of these reactors in such a way that it has at least two different zones. Such zones can differ for example in reaction conditions such as, for example, the temperature or the pressure and/or in the geometry of the zone, such as, for example, the volume or the cross section. If the reaction is carried out in two or more reactors, two or more identical reactor types or at least two different reactor types can be used. In particular, the reaction with dinitrogen monoxide is carried out in a single reactor. For example, the reaction can take place in a continuous procedure or in a batch procedure.

The residence time of the reaction mixture in the reactor is generally in the range from 0.1 to 40 hours, preferably in the range from 1 to 30 hours, further preferably in the range from 2 to 25 hours.

In the feed, the molar ratio of dinitrogen monoxide and the cyclic olefin is generally in the range from 0.01 to 30, such as e.g. in the range from 0.03 to 10, particularly preferably in the range from 0.05 to 1 and very particularly preferably in the range from 0.08 to 0.2.

Since dinitrogen monoxide is preferably used in deficit, only some of the cyclohexadeca-1,9-diene (XI) is reacted. Unreacted cyclohexadeca-1,9-diene is separated from the reaction product by distillation and returned again to the reaction. Here, the unreacted cyclohexadeca-1,9-diene is produced as top product and the reaction product is produced as bottom product of the column. The distillation takes place here at a top pressure of 20 mbar and a bottom temperature of 210° C. The pressure difference over the column was 18 mbar. The column was equipped with structured fabric packing of the Montz A3 type. The packing height was 4 m and the feed was at 2 m. The compound X was then isolated from the resulting bottom discharge by distillation as secondary component (see example 1).

The desired reaction product is produced here as secondary component, meaning that the reaction mixture has to be purified in a suitable manner. This can take place e.g. by distillation (such as in particular by fractional distillation, preferably at reduced pressure) or chromatographically. Suitable purification methods are known to the person skilled in the art. The purification can take place e.g. batchwise or else continuously.

For example, the distillation by means of distillation column with packings known to the person skilled in the art can be used. The optimum distillation conditions can be ascertained by the person skilled in the art without unreasonable effort. The distillation can be carried out in particular in vacuo, for example at a pressure <1000 mbar, <500 mbar, <300 mbar, <100 mbar or <10 mbar. The distillation column used can have a plurality of, such as e.g. at least 20, at least 25 or at least 30, theoretical plates, such as e.g. up to 70 plates. The reflux ratio can be e.g. in the range from about 5 to 100 and can be at least 20, at least 25 or at least 30 and is in particular about 100 for a particularly advantageous fractionation.

For example, a column chromatography can also take place instead of or following a distillative purification. For this, column materials and eluents known to the person skilled in the art are used. The optimum chromatography conditions, such as column geography and rate of eluent, can be ascertained by the person skilled in the art without unreasonable effort.

Examples of suitable column materials are polar adsorption agents such as e.g. iron oxide $Fe_2O_3$, aluminum oxide, carbohydrates or silica gel with or without additives such as e.g. fluorescence indicators or gypsum.

Examples of suitable eluents are: aliphatic or aromatic eluents, such as e.g. alkanes or cycloalkanes, such as e.g. pentane, petroleum ether, hexane, heptane, toluene or the corresponding cyclic compounds; aliphatic ethers, esters, such as e.g. $Et_2O$, MTBE, EtOAc, acetone, or mixtures of such eluents, such as e.g. hexane/MTBE, hexane/EtOAc, pentane/$Et_2O$, petroleum ether/$Et_2O$.

In this process, a desired carbaldehyde of the formula X, or mixtures thereof, can be isolated in pure form or in a purity of more than 20, such as e.g. more than 30, more than 40, more than 50, more than 60, more than 60 or more than 80% by weight.

The carbaldehyde of the formula X can be isolated here in stereoisomerically pure form, or in particular as a mixture of two or more stereoisomers, particularly if radical A has a C=C double bond.

In particular, aromatic substances comprising trans- and cis-cyclopentadec-8-enylcarbaldehyde (I, III) and/or trans-cyclopentadec-7-enylcarbaldehyde (II) are accessible by this route.

Synthesis Route 2: Multistage Carbaldehyde Synthesis Via Wolff Rearrangement

Starting from the corresponding, cycloaliphatic aldehyde, in particular a cyclic mono- or polyunsaturated ketone XII (i.e. compared to the cyclic radical A in the product of the formula X, starting compound XII comprises an additional ring carbon atom), compounds of the formula X are accessible in a multistage process. The individual synthesis stages are known per se to the person skilled in the art in the field of organic synthesis.

Examples of suitable starting compounds (which can be used both in stereoisomerically pure form as well as in the form of stereoisomer mixtures) for the preparation of compounds of the formula (X), in which A is a monounsaturated C$_{15}$ radical, comprise Globanone®, as available e.g. from Symrise.

a) Stage 1: Formylketone Preparation

Corresponding reactions are described e.g. in: Wu, Z.; Li, Y.; Cai, Y.; Yuan, J.; Yuan, C., *Bioorganic & Medicinal Chemistry Letters* 2013, 23, 4903-4906; or Prelog, V.; Ruzieka, L.; Metzler, O, *HELV. CHIM. ACTA* 1947, 30, 1883-1895.

A suitable reaction vessel with reflux condenser is charged, under an inert gas atmosphere, with a suspension of a suitable hydride such as e.g. NaH, in organic phase, such as e.g. DMF. At reduced temperature, such as e.g. 0 to 10° C., a solution of the cycloaliphatic ketone, such as e.g. of the monounsaturated cyclic C$_{16}$ ketone globanone (XII), is added dropwise to this suspension, e.g. over a period of 1 to 5 hours. The ketone is used in an approximately equimolar amount, but in particular in a slight (e.g. 1.1- to 1.5-fold) molar deficit, based on the hydride. To complete the deprotonation, the temperature can be increased and the reaction mixture can be held at this temperature over a suitable time period, e.g. for the period from 1 to 4 h at 40 to 80° C., such as e.g. 2 h at 60° C. The reaction mixture is then cooled again, e.g. to 0 to 10° C. The addition of a solution of methyl formate in a suitable solvent, such as e.g. DMF, then takes place. Methyl formate is used in an approximately equimolar amount, but in particular in a slight (e.g. 1.1- to 1.5-fold) molar excess, based on the ketone. The reaction mixture is stirred over a suitable period, such as e.g. 5 to 30 h, such as e.g. about 16 h at ambient temperature, and the reaction is then ended by adding ice-water. The mixture is washed with ether, e.g. MTBE, and the organic phases are discarded. By adding sulfuric acid, the aqueous phase is acidified, e.g. to pH 2, and extracted several times with ethyl acetate. The combined ethyl acetate phases are dried over Na$_2$SO$_4$ and then concentrated in vacuo. The residue thus obtained consists predominantly of the desired regioisomeric formyl ketones XIII or the tautomeric enols thereof and is used without further work-up in the subsequent stage.

b) Stage 2: Diazoketone Preparation

Corresponding reactions are described e.g. in Regitz, M. and Ruter, J., *Chem. Ber.* 1968, 101, 1263-1270.

Added dropwise with cooling, e.g. to −20 to 0° C., in particular at −10° C. over a period of several hours, such as e.g. 2 to 8 h, to a solution, charged to a suitable reaction vessel, of the crude product from preceding stage 1 and triethylamine (in particular in molar excess, such as e.g. 1.5- to 2-fold excess) in a suitable solvent, in particular in a halogenated hydrocarbon, such as dichloromethane, is a solution of 4-acetamidobenzyl azide (in molar excess, such as e.g. 1.5- to 2-fold excess) in the same solvent. In principle, other diazo transfer reagents are also suitable, such as toluenesulfonyl azide. Optionally after leaving the reaction mixture to stand at elevated temperature, such as e.g. room temperature, and solvent exchange (e.g. dichloromethane for MTBE), the organic phase is washed with sodium hydroxide solution and the aqueous phase is extracted twice with the organic solvent, e.g. MTBE. The combined organic phases, comprising the desired diazo ketone XIV (optionally as isomer mixture), are dried over Na$_2$SO$_4$ and further reacted as described below.

c) Stage 3: Wolff Rearrangement and Esterification of the Ketene Formed Therein:

Corresponding reactions are described e.g. in Regitz, M. and Ruter, J., *Chem. Ber.* 1968, 101, 1263-1270, or Kirmse, W., *Eur. J. Org. Chem.* 2002, 14, 2193-2256.

A solution of the diazo ketone XIV from stage 2 is slowly added dropwise over a period of 5 to 20 h, such as e.g. 10 h, to heated alkanol, such as e.g. heated 1-hexanol (e.g. 150° C.), charged to a reaction vessel provided with distillation bridge. With controlled N$_2$-formation, the organic solvent is simultaneously removed by distillation. At the end of the evolution of gas, the reaction mixture is cooled and then remains of solvent and alkanol are removed in vacuo, giving the desired cyclic ester XV with an aliphatic ring smaller by 1 carbon atom (optionally in the form of an isomer mixture).

d) Stage 4: Ester Reduction to the Alcohol

Corresponding reactions are described e.g. in March, J. "Advanced organic Chemistry", 4th edition, John Wiley & Sons, New York 1992.

A reducing agent, e.g. a solution of diisobutylaluminum hydride (DIBAL-H) in molar excess (e.g. 1.5- to 3-fold), is added dropwise to a solution of the ester XV from stage 3 in an inert, organic apolar solvent, such as e.g. toluene, charged to a chilled reaction vessel, e.g. at −78° C. The cooling is removed and after leaving to stand at ambient temperature, the reaction is ended, such as e.g. by adding ethyl acetate and a saturated aqueous K,Na tartate solution. The aqueous phase is extracted with ethyl acetate, the combined organic phases are dried over Na$_2$SO$_4$ and are concentrated in vacuo, giving the corresponding cyclic alcohols XVI (optionally in the form of an isomer mixture).

e) Stage 5: Alcohol Oxidation to the Carbaldehyde:

Corresponding reactions are described e.g. in March, J. "Advanced organic Chemistry", 4th edition, John Wiley & Sons, New York 1992.

In succession, kieselguhr and an oxidizing agent suitable for primary alcohols, such as e.g. HOCl, pyridinium dichromate or in particular pyridinium chlorochromate (PCC) (in approximately equimolar amounts), are added to a solution of the reaction product from stage 4 in a suitable solvent, such as e.g. dichloromethane. Following reaction for several hours, e.g. 3-6 h at ambient temperature, the reaction mixture is filtered over silica gel and concentrated in vacuo. This gives the desired aldehyde X (optionally in the form of an isomer mixture).

e) Stage 6 (Optional) Column Chromatography

For this, column materials and eluents known to the person skilled in the art are used. The optimum chromatography conditions, such as column geometry and rate of eluent, can be ascertained by the person skilled in the art without unreasonable effort.

Examples of suitable column materials are polar adsorption agents such as e.g. iron oxide Fe$_2$O$_3$, aluminum oxide, carbohydrates or silica gel with or without additives such as e.g. fluorescence indicators or gypsum.

Examples of suitable eluents are: aliphatic or aromatic eluents, such as e.g. alkanes or cycloalkanes, such as e.g. pentane, petroleum ether, hexane, heptane, toluene or the corresponding cyclic compounds; aliphatic ethers, esters or ketones, such as e.g. MTBE, Et$_2$O, EtOAc or acetone, or mixtures of such eluents such as e.g. hexane/MTBE, hexane/EtOAc, pentane/Et$_2$O, petroleum ether/Et$_2$O.

In the process, a desired carbaldehyde, or mixtures thereof, can be isolated in pure form or in a purity of more than 20, such as e.g. more than 30, more than 40, more than 50, more than 60, more than 60 or more than 80% by weight.

The carbaldehyde can be present here in stereoisomerically pure form, or in particular as a mixture of two or more stereoisomers.

In particular, aromatic substances comprising trans-cyclopentadec-8-enylcarbaldehyde (I) and/or cis-cyclopentadec- 8-enylcarbaldehyde (III), and/or trans-cyclopentadec-7-enylcarbaldehyde (II), in particular ternary mixtures thereof, are accessible by this route.

The invention will now be explained in more detail by reference to the following nonlimiting working examples:

EXPERIMENTAL SECTION

Methods:
Gas Chromatography (GC)
Separating column: CP-Wax 52CB 25 m×0.32 mm×1.2 µm 1 ml/min $N_2$
Conditions: 90°-5 min-10°/min-240°-30 min Inj/Det 200®/250° (method A)
Conditions: 80°-3°/min-250°-Inj/Det 200°/250° (method B) (only example 2)
Sample volume: 0.2 ml
GC/MS
Separating column: CP-Wax 52 CB (1.2 µm film thickness), splitting ratio 10:1
Conditions: 80°-3 min-240°-30 min 0.2 µl
MS conditions: 25-785 amu, 70 eV
GC/IR
Detector: MCT/A wavelength 650-4000 $cm^{-1}$
Cell/transfer temperature 250° C.
Scan 6
Resolution 8
Column Chromatography
A glass column with fritte base was used. The column was packed to ⅔ with slurried silica gel $F_{254}$. The solvent mixture was pushed through the column at a superatmospheric pressure of 0.2-0.4 bar.

Example 1: $C_{15}$-Aldehyde Synthesis by $N_2O$ Oxidation of 1,9-Cyclohexadecadiene In an adiabatic tubular reactor (3 m in length, diameter 6 cm, reactor volume 9 l) filled with Raschig rings made of 1.4541 stainless steel, 2000 g/h of 1,9-cyclohexadecadiene (cis/trans-isomer mixture) were reacted with 52 ml/h an $N_2O/CO_2$ mixture (15% $CO_2$ fraction) at a reactor feed temperature of 216° C. Molar ratio olefin/$N_2O$: 9-10. Unreacted 1,9-cyclohexadecadiene was separated off distillatively by means of a distillation column (Montz fabric packing A3, separation-effective height 4000 mm, internal diameter 55 mm, feed at half height of the column) at a bottom temperature of 210° C. and a top pressure of 20 mbar. The bottom discharge comprises approx, 5% by weight of the $C_{15}$-aldehydes (I) ($t_{Ret}$=23.3 min GC method A), (II) ($t_{Ret}$=23.7 min) and (III) ($t_{Ret}$=24.1 min) and less than 1% by weight of 1,9-cyclohexadecadiene ($t_{Ret}$=18.2, 18.5, 18.9 min; 3 isomers) (main component in the bottom is globanone; $t_{Ret}$=24.4, 24.8 min, 2 isomers).

Example 2 $C_{15}$-Aldehyde Synthesis by $N_2O$ Oxidation of 1,9-Cyclohexadecadiene A mixture consisting of cyclohexadeca-1,9-diene (isomer mixture, sum of the isomers approx. 98%, 20 g) and cyclohexane (80 g) was mixed in a 300 ml autoclave. The autoclave was sealed and compressed with nitrogen to 50 bar and then decompressed again. The process was repeated three times. After the last decompression, the autoclave was compressed with $N_2O$ to 30 bar, molar ratio olefin/$N_2O$ 250-270, then the stirrer was switched on (at 400 rpm) and the autoclave was heated to the reaction temperature over the course of an hour. The mixture was stirred for 12 h at 220° C. The system was then cooled to room temperature, the autoclave was decompressed and the crude discharge analyzed by GC. In total, the discharge comprised 2,2% by weight of trans-cyclopentadec-8-enylcarbaldehyde (I) ($t_{Ret}$=23.3 min), trans-cyclopentadec-7-enylcarbaldehyde (II) ($t_{Ret}$=23.7 min) and cis-cyclopentadec-8-enylcarbaldehyde (III) ($t_{Ret}$=24.1 min).

Example 3: Enrichment of $C_{15}$-Aldehydes by Fractional Distillation 2600 g of a mixture (crude discharge from oxidation of cyclohexadeca-1,9-diene with $N_2O$; see example 1) with in total approx. 5% trans-cyclopentadec-8-enylcarbaldehyde (I), trans-cyclopentadec-7-enylcarbaldehyde (II) and cis-cyclopentadec-8-enylcarbaldehyde (III) were fractionally distilled in a batch column (Sulzer fabric packing DX, separation-effective height 2000 mm, diameter 43 mm, top pressure: 5 mbar, pressure loss over column: 5 mbar, bottom temperature: 180° C., Sambay evaporator, reflux ratio: 100). The mixture of trans-cyclopentadec-8-enylcarbaldehyde (I) ($t_{Ret}$=23.3 min), trans-cyclopentadec-7-enylcarbaldehyde (II) ($t_{Ret}$=23/min) and cs-cyclopentadec-8-enylcarbaldehyde (III) ($t_{Ret}$=24.1 min) was able to be enriched in the process in different fractions to 29, 33 and 46% by weight. The respective content was determined by gas chromatography (boiling point of the fractions 160, 167 and 167° C.)

Example 4: Purification by Column Chromatography 2.05 g of a mixture of trans-cyclopentadec-8-enylcarbaldehyde (I), trans-cyclopentadec-7-enylcarbaldehyde (II) and cis-cyclopentadec-8-enylcarbaldehyde (III) with a content total of 33% by weight (cf. example 3) were purified by means of column chromatography (silica gel, glass column with fritte base, superatmospheric pressure of 0.2 bar) using an eluent mixture of cyclohexane/MTBE (50:1 and 40:1). Following chromatographic purification, 100 mg of trans-cyclopentadec-8-enylcarbaldehyde (I) ($t_{Ret}$=23.494 min) were isolated with a purity of 83%.

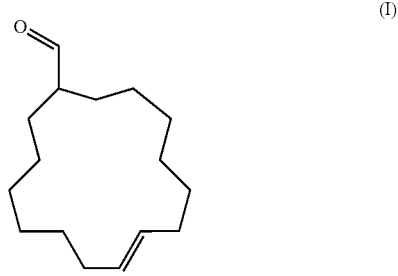 [SMILES: O=CC1CCCCCC/C=C/CCCCCC1]

(I)

$^1$H NMR (500 MHz, $CDCl_3$, 25° C.): σ=9.5 (s, CHO, 1H), 5.4-5.3 (m, HC═CH, 2H), 2.4-2.3 (m, 1H), 2.2-1.9 (m, 4H), 1.7-1.6 (m, 2H), 1.5-1.1 (m, 18H).

$^{13}$C-NMR (125 MHz, $CDCl_3$, 25° C.): σ=206.0 (C═O), 131.2 (HC═CH), 48.4 (CH), 31.6 (2×$CH_2$), 28.3 (2×$CH_2$), 27.0 (2×$CH_2$), 26.7 (2×$CH_2$), 26.6 (2×$CH_2$), 25.1 (2×$CH_2$).

IR (GC/IR) υ [$cm^{-1}$]=3029 (1,2 trans subst. DB), 2934, 2865, 2797, 2695, 1738 (CHO), 1454, 1353, 1110, 968 (1,2 trans subst. DB).

Example 5; C15-Aldehyde Synthesis Via Wolff Rearrangement a) Stage 1:

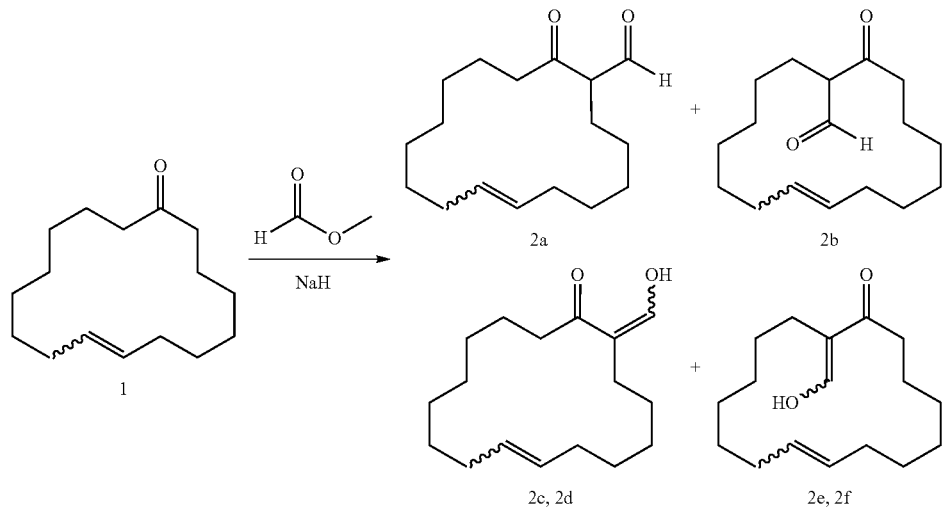

In a three-necked flask with reflux condenser and mechanical stirrer, NaH (60% by weight in mineral oil, 33.5 g, 0.84 mol, 1.1 eq.) is introduced under an argon atmosphere and suspended in DMF (DMF=N,N-dimethylformamide, 50 ml). At 0° C., a solution of globanone (1, 150 g, 0.64 mol, 1.3 eq.) in dry DMF (250 ml) is added dropwise to this suspension over a period of 3.5 h. To complete the deprotonation, the mixture is heated at 60° C. for 2 h and then cooled to 0° C. After adding a solution of methyl formate (57 g, 0.95 mol, 1.5 eq.) in DMF (50 ml), the mixture is stirred for 16 h at ambient temperature and the reaction is then ended by adding ice-water. The mixture is washed twice with MTBE (MTBE: Methyl tert-butyl ether) and the organic phases are discarded. The aqueous phase is brought to pH 2 by adding sulfuric acid (50% strength by weight) and extracted several times with ethyl acetate. The combined ethyl acetate phases are dried over $Na_2SO_4$ and then concentrated in vacuo. The residue thus obtained (134 g) consists, according to NMR, to about 90% of the desired regioisomeric formyl ketones 2a and 2b and/or the tautomeric enols thereof (2c-2f) and is used without further work-up in the subsequent stage.

b) Stages 2 and 3:

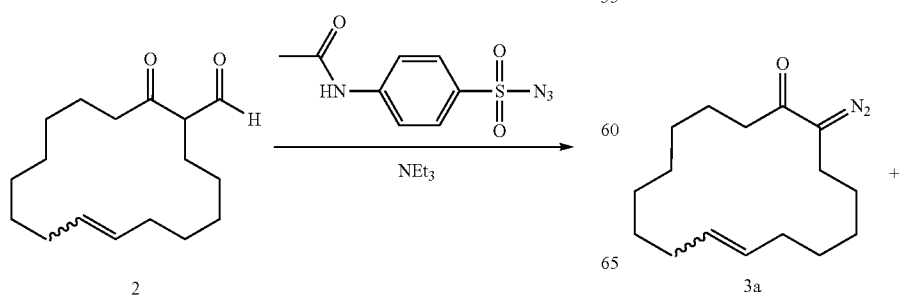

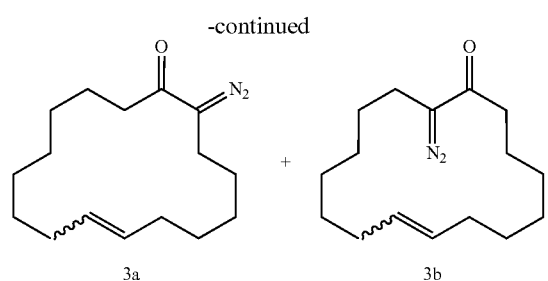

At −10° C., a solution of 4-acetamidobenzyl azide (97.3 g, 0.41 mol, 0.9 eq.) in dichloromethane (400 ml) is added dropwise to a solution of the crude product (2a-f) from the preceding stage 1 (134 g purity about 90%, 0.46 mol, 1 eq.) and triethylamine (86.6 g, 0.86 mol, 1.9 eq.) in dichloromethane (100 ml) over a period of 4 h. After 20 h at RT, MTBE (400 ml) is added and the dichloromethane is distilled off. The organic phase is washed with sodium hydroxide solution (6% by weight) and the aqueous phase is extracted twice with MTBE. The combined MTBE phases are dried over $Na_2SO_4$ and further reacted as described below.

-continued

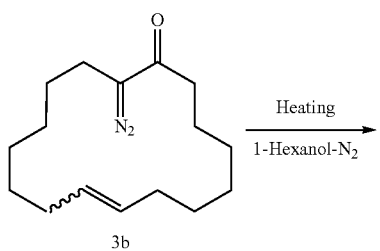
3b

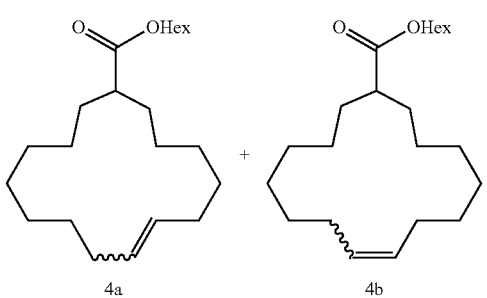
4a  4b

Hex: Hexyl

The solution of the diazoketone 3 in MTBE is slowly added dropwise over a period of 10 h to 1-hexanol (300 ml) heated to 150° C. such that the $N_2$ formation remains controllable and at the same time the introduced MTBE can be distilled off continuously via a distillation bridge. At the end of the gas evolution, the reaction mixture is cooled and then remains of MTBE and the 1-hexanol are removed in vacuo. This gives 92 g of a yellow, viscous residue which, according to NMR, comprises 60-70% of the esters 4a and 4b as isomer mixture.

c) Stage 4:

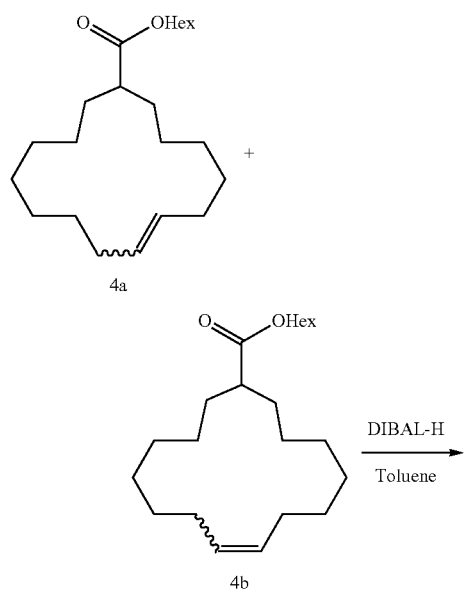
4a

4b

-continued

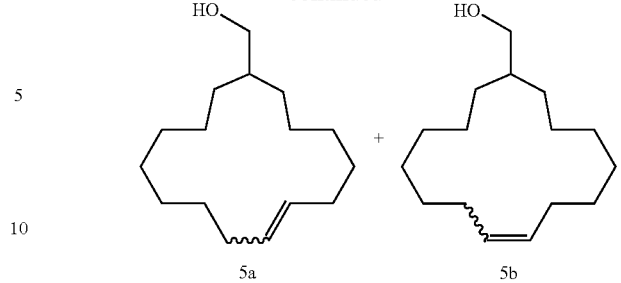
5a  5b

DIBAL-H: diisobutylalluminum hybrid

At −78° C., a solution of diisobutylaluminum hydride (DIBAL-H) in heptane (c=1 mol/l, 490 ml, 0.5 mol, 2.5 eq.) is added dropwise to a solution of the ester (4a and 4b) (92 g, 70% purity, 0.2 mol, 1 eq.) in toluene (130 ml). The cooling is removed and, after 2 h at ambient temperature, the reaction is ended by adding ethyl acetate (50 ml) and saturated aqueous K,Na tartrate solution (400 ml). The suspension is stirred until the clouding has cleared at room temperature. The aqueous phase is extracted with ethyl acetate, the combined organic phases are dried over $Na_2SO_4$ and concentrated in vacuo. 77 g of the isomeric alcohols 5a and 5b are obtained as a colorless oil.

d) Stage 5:

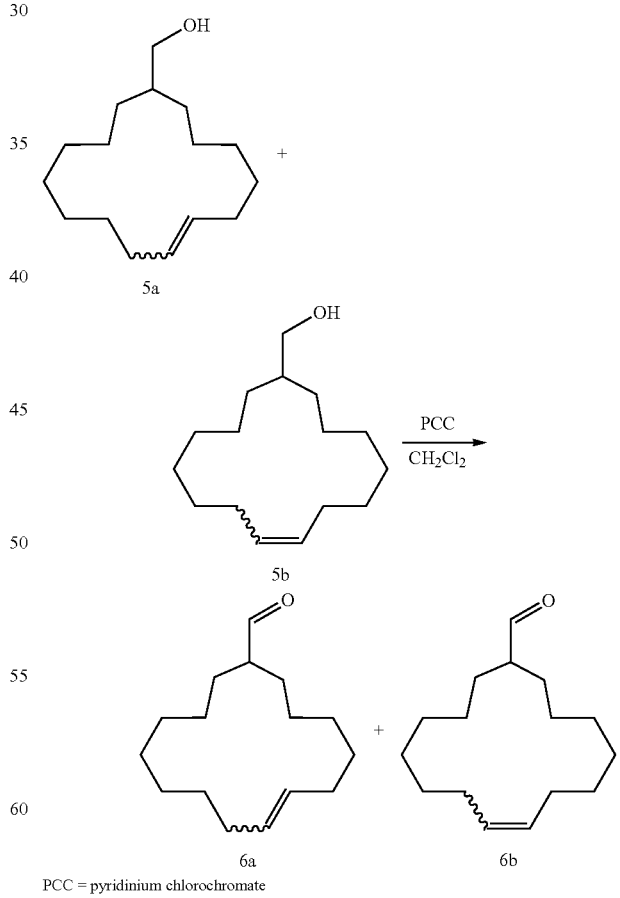
5a

5b 6a  6b

PCC = pyridinium chlorochromate

In succession, kieselguhr (30 g) and pyridinium chlorochromate (PCC) (30 g, 0.14 mol, 1 eq.) are added to a solution of half of the crude mixture from the preceding stage 4 (33 g, 0.14 mol, 1 eq.) in dichloromethane (300 ml). After 4 h at ambient temperature, the reaction mixture is filtered over silica gel and concentrated in vacuo. 21 g of the isomeric aldehydes 6a and 6b are obtained in a purity of 70% (71 mmol, total yield over five stages starting from globanone 22%).

To assess the olfactory properties, some of the crude product is purified by column chromatography.

e) Stage 6 (Column Isolation I, II and III)

5.0 g of a mixture of the aldehydes 6a and 6b from stage 5 with a content, according to GC, in total of 70% by weight were purified by means of chromatography using an eluent mixture of cyclohexane/MTBE (60:1-40:1). Following chromatographic purification, 1 g of a mixture of trans-cyclopentadec-8-enylcarbaldehyde (I), trans-cyclopentadec-7-enylcarbaldehyde (II) and cis-cyclopentadec-8-enylcarbaldehyde (III) was isolated with a purity of 87% (total of (I)+(II)+(III) in the ratio 46:24:29).

f) Analytical Results:

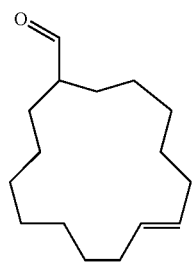
(II)

IR (GC/IR) υ [cm$^{-1}$]=3023 (trans 1,2 subst. DB), 2934, 2864, 2801, 2696, 1738 (CHO), 1454, 968 (trans 1,2 subst. DB).

MS (GC/MS-IR coupling) m/z=236.

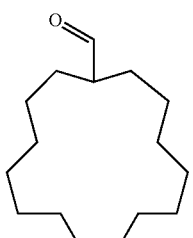
(III)

IR (GC/IR) υ [cm$^{-1}$]=3012 (1,2 cis subst., DB), 2935, 2866, 2801, 2698, 1738 (CHO), 1457, 719 (1,2 cis subst. DB).

MS (GC/MS-IR coupling) m/z=236.

NMR Data of the Mixture (II) and (III):

$^{1}$H NMR (500 MHz, CDCl$_3$, 25° C.): σ=9.6 (s, 2H, 2×CHO), 5.4-5.2 (m, 4H, 2×HC═CH), 2.5-1 (m, 50H).

$^{13}$C-NMR (125 MHz, CDCl$_3$, 25° C.): σ=205.4 (CHO), 205.3 (CHO), 131.4, 131.0, 130.2 (2×CH$_{ar}$), 50.4 (CH$_{alk}$), 49.9 (CH$_{alk}$), 31.7-24.4 (24×CH$_2$).

FIG. 1 shows the GC/IR spectra of the compounds I, II and III according to the invention (referred to therein as components 1, 2 and 3).

Example 6: Olfactory Assessment

1) Assessment of Different Mixtures of the Aldehydes I, II and III

Composition of the Investigated Samples:

No. 1: (I):(II):(III)=46:24:29; purity=87.5% (total (I-III)) (cf. example 5, after stage 6)

No. 2: (I):(II):(III)=43:24:33; purity=77.8% (total (I-III))

Result

Sample No. 1:

Smelling strip test <1 min musk

Smelling strip test 30 min musk

Smelling strip test 1 h musk

Smelling strip test 24 h musk

Sample No. 2:

Smelling strip test <1 min musk (significantly more intensive than sample No. 1)

Smelling strip test 30 min musk (significantly more intensive than sample No. 1)

Smelling strip test 1 h musk (significantly more intensive than sample No. 1)

Smelling strip test 24 h musk (significantly more intensive than sample No. 1)

The mixtures of the aldehydes (I-III) have a musk-like odor note.

2) Assessment of Aldehyde I;

Composition of the Sample (I):(II):(III)=93:2:4; purity=89.4% (total (I-III)) (cf. example 4)

Result:

Smelling strip test <1 min musk, considerably soapy, green, gassy

Smelling strip test 10 min musk, considerably soapy, green, gassy

Smelling strip test 30 min musk, considerably soapy, green, gassy

Smelling strip test 1 h musk, considerably soapy, green, gassy

Smelling strip test 24 h musk

The pure substance (I) also has a considerably soapy, green and gassy odor besides the musk-like odor note.

Reference is made expressly to the disclosure of the documents mentioned herein.

The invention claimed is:

1. A carbaldehyde of the formula X

(X)

wherein A is a cycloaliphatic, monocyclic unsubstituted hydrocarbon radical, the carbaldehyde selected from isomeric formulae I, II or III,

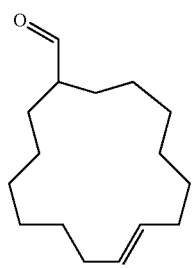 (I)

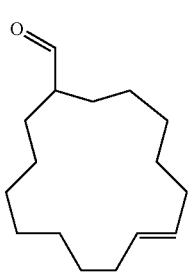 (II)

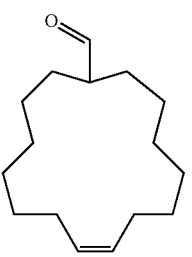 (III)

and the stereoisomeric forms thereof.

2. A composition comprising at least one carbaldehyde according to claim 1.

3. An aromachemical composition comprising at least one carbaldehyde of the formula X

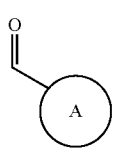 (X)

wherein A is a cycloaliphatic, monocyclic, unsubstituted hydrocarbon radical with 15 ring carbon atoms, and n C=C double bonds, where n is 1, 2 or 3.

4. The aromachemical composition according to claim 3, wherein n is 1.

5. The aromachemical composition according to claim 3, where the compound is selected from the isomeric compounds of formulae I, II, or III

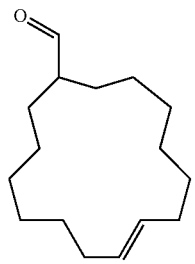 (I)

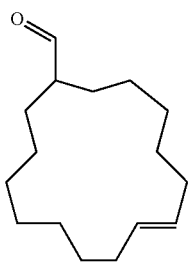 (II)

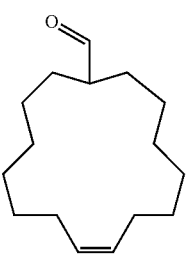 (III)

and the stereoisomeric forms thereof.

6. A product selected from the group consisting of perfumes, detergents, cleaners, cosmetic products, body care products, hygiene articles, foods, food supplements, air fresheners, scent substances, pharmaceutical products and crop protection products that contains the aromachemical composition according to claim 3.

7. The aromachemical composition according to claim 3 comprising trans-cyclopentadec-8-enylcarbaldehyde of the formula (I).

8. The aromachemical composition according to claim 7 further comprising trans-cyclopentadec-7-enylcarbaldehyde of the formula (II) and cis-cyclopentadec-8-enylcarbaldehyde of the formula (III), where the fraction of trans-cyclopentadec-8-enylcarbaldehyde in the composition, based on a total sum of the formulae I, II and III is at least 65%.

9. The aromachemical composition according to claim 7 comprising the compounds of the formulae I, II and III, where the weight ratio of I:II:III is in the range from 0.3-0.5:0.2-0.3:0.3-0.4.

10. The aromachemical composition according to claim 9, wherein the weight ratio of I:II:III is about 43:24:33.

11. A process for preparing a compound of formula X

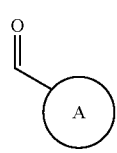 (X)

wherein A is a cycloaliphatic, hydrocarbon radical with in ring carbon atoms and n C═C double bonds, where in is an integer selected from 13, 14, 15, 16 or 17, and n is selected from 1, 2 or 3, where a) reacting a cycloaliphatic compound of the formula XII

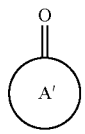
(XII)

wherein A' is a cycloaliphatic hydrocarbon radical with m+1 ring carbon atoms, where m is an integer selected from 13, 14, 15, 16 or 17, and optionally has n+1 C═C double bonds, where n is selected from 1, 2 or 3, with NaH and methyl formate to give the corresponding cyclic formyl ketone XIII

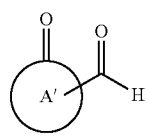
(XIII)

in which A' is as defined above;

b) reacting the cyclic formyl ketone with triethylamine and 4-acetamidobenzyl azide to provide the corresponding diazoketone XIV

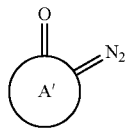
(XIV)

in which A' is as defined above;

c) removing the $N_2$ from the diazoketone under the conditions in a Wolff rearrangement, $N_2$ is cleaved off in the presence of an alkanol to provide the corresponding ester of formula XV

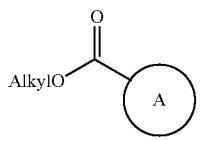
(XV)

in which A is as defined above;

d) reducing the ester of formula XV to the corresponding alcohol of formula XVI

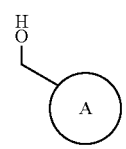
(XVI)

in which A is as defined above;

e) oxidizing the alcohol of formula XVI to give the carbaldehyde of the formula X; and f) optionally, isolating the carbaldehyde of the formula X from the reaction mixture.

12. The process according to claim 11, wherein the compound of the formula XII in stage a) is cis-/trans-cyclohexadec-8-enone, and trans-cyclopentadec-8-enylcarbaldehyde (I), trans-cyclopentadec-7-enylcarbaldehyde (ii) and cis-cyclopentadec-8-enylcarbaldehyde (III) are obtained in stage a).

13. The process according to claim 11, where compounds of the formulae (I), (II), or (III), or mixtures thereof, are obtained in stage f) by chromatic purification of a reaction mixture from stage e), wherein the total amount of (I), (II) and (III) in a mixture following stage e) is at least 50% by weight.

14. The aromachemical composition according to claim 2 comprising 0.01 to 99.9% by weight of the carbaldehyde of the formula X

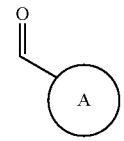
(X)

wherein A is a cycloaliphatic, monocyclic unsubstituted hydrocarbon radical, the carbaldehyde selected from isomeric formulae I, II or III,

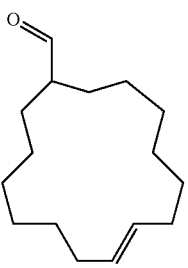
(I)

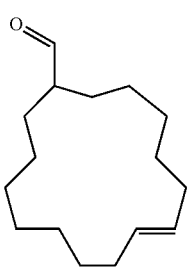
(II)

(III)
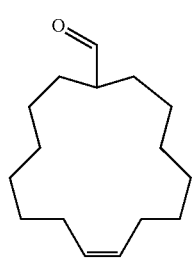
and the stereoisomeric forms thereof, based on the total weight of the composition.
* * * * *